(12) United States Patent
Sitzman et al.

(10) Patent No.: US 6,801,802 B2
(45) Date of Patent: Oct. 5, 2004

(54) SYSTEM AND METHOD FOR SELECTING PHYSIOLOGICAL DATA FROM A PLURALITY OF PHYSIOLOGICAL DATA SOURCES

(75) Inventors: David A. Sitzman, Hubertus, WI (US); Robert M. Farrell, Brown Deer, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 230 days.

(21) Appl. No.: 09/896,076

(22) Filed: Jun. 29, 2001

(65) Prior Publication Data

US 2003/0009106 A1 Jan. 9, 2003

(51) Int. Cl.$^7$ ............................................. A61B 5/0402
(52) U.S. Cl. ....................... 600/513; 600/519; 600/515
(58) Field of Search ................................. 600/513, 515, 600/519, 483, 301, 522, 502

(56) References Cited

U.S. PATENT DOCUMENTS

| | | | |
|---|---|---|---|
| 3,608,545 A | * 9/1971 | Novack et al. ............ | 600/513 |
| 4,860,759 A | * 8/1989 | Kahn et al. ................ | 600/481 |
| 5,331,549 A | * 7/1994 | Crawford, Jr. ............. | 600/513 |
| 5,353,793 A | * 10/1994 | Bornn ........................ | 600/386 |
| 5,626,140 A | * 5/1997 | Feldman et al. ............ | 600/484 |
| 2003/0023178 A1 | * 1/2003 | Bischoff et al. ............ | 600/515 |

OTHER PUBLICATIONS

Journal of Clinical Monitoring, 13; 379–384, *A Robust Sensor Fusion Improves Heart Rate Sttimation: Clinical Evaluation*, 1997, 6 sheets.
Journal of Clinical Monitoring, 13; 385–393, *A Robust Sensor Fusion Method for Heart Rate Estimation*, 1997, 9 sheets.
Partial European Search Report; European Application No. 02254543.8; mailed Oct. 27, 2003.

* cited by examiner

*Primary Examiner*—Kennedy Schaetzle
(74) *Attorney, Agent, or Firm*—Andrus, Sceales, Starke & Sawall, LLP (57) ABSTRACT

A system for selecting physiological data from a plurality of physiological data sources includes first and second physiological data sources and a selection algorithm. The first physiological data source is configured to provide first physiological data. The first physiological data includes a first measurement of a physiological trait. The second physiological data source is configured to provide second physiological data. The second physiological data includes a second measurement of the physiological trait. The first and second measurements are based on different physiological characteristics. The selection algorithm is configured to receive the first and second physiological data and to select one of the first and second measurements as the output data for the physiological trait based on at least one of the first physiological data and the second physiological data.

22 Claims, 5 Drawing Sheets

SYSTEM AND METHOD FOR SELECTING PHYSIOLOGICAL DATA FROM A PLURALITY OF PHYSIOLOGICAL DATA SOURCES

BACKGROUND OF THE DISCLOSURE

Patient monitors routinely process signals acquired from patients and provide a caregiver or clinician with computed estimates of features contained within those signals. In the case of ECG (electrocardiogram) signals, those features include heart rate and arrhythmias (i.e., disturbances in the normal cardiac rhythm).

One function of a patient monitor is to provide alarm mechanisms to alert the user when the patient's heart rate is outside of prescribed limits, or when arrhythmias occur. However, the presence of noise in the acquired ECG signal, due to a multiplicity of causes, results in a significant false positive alarm rate for these alarm conditions. Such false alarm rates decrease clinician productivity and satisfaction, and decrease the effectiveness of clinical alarm mechanisms.

One attempt at solving the problems of false positive alarms is a method that discriminates between good and bad sensor measurements and combines only the good readings to derive an optimal heart rate estimate. A Kalman filter is used to derive a fused estimate. However, the computational overhead required to filter readings using Kalman filter techniques from several sensors is extensive, and is ill-suited for many applications. Also, the use of a combined estimate of heart rate decreases the likelihood of acceptance by clinicians.

Accordingly, what is needed is an improved system and method for selecting physiological data from a plurality of physiological data sources. Further, what is needed is a system and method that improves the accuracy of a physiological output by selecting from among existing solutions, thereby reducing computational overhead and improving the likelihood of acceptance by clinicians. Further still, what is needed is a system and method for providing a more accurate estimate of patient heart rate, and a more accurate determination of alarm conditions, such as heart rate limit detection and arrhythmia. Such a system would decrease the number of false positive alarms, thereby providing a more intuitive and useful system for clinicians. Further yet, what is needed is a system and method for monitoring physiological signals of a patient that improves the clinical performance of the patient monitor, improves clinician productivity, improves patient care, and reduces product support costs.

The teachings hereinbelow extend to those embodiments which fall within the scope of the appended claims, regardless of whether they accomplish one or more of the above-mentioned needs.

SUMMARY OF EXEMPLARY EMBODIMENTS

According to one exemplary embodiment, a system for selecting physiological data from a plurality of physiological data sources includes first and second physiological data sources and a selection algorithm. The first physiological data source is configured to provide first physiological data. The first physiological data includes a first measurement of a physiological trait. The second physiological data source is configured to provide second physiological data. The second physiological data includes a second measurement of the physiological trait. The first and second measurements are based on different physiological characteristics. The selection algorithm is configured to receive the first and second physiological data and to select one of the first and second measurements as the output data for the physiological trait based on at least one of the first physiological data and the second physiological data.

According to another exemplary embodiment, a system for improving the accuracy of an arrhythmia detection algorithm includes an ECG data source, an arrhythmia detection algorithm, a hemodynamic heart rate data source and an alarm algorithm. The ECG data source is configured to receive ECG signals from an ECG sensor and to generate ECG heart rate data based on the received ECG signals. The arrhythmia detection algorithm is configured to receive the physiological data and to detect an arrhythmia condition. The hemodynamic heart rate data source is configured to receive signals from a hemodynamic heart rate sensor and to generate hemodynamic heart rate data based on the received signals. The alarm algorithm is configured to receive the ECG heart rate data and the hemodynamic heart rate data and to provide an alarm signal based on the detected arrhythmia condition and the hemodynamic heart rate data.

According to yet another exemplary embodiment, a system for improving the accuracy of a heart rate limit alarm includes first and second heart signal sources and an alarm algorithm. The first heart signal source is configured to receive first signals from a first sensor and to generate a first heart rate based on the first signals. The second heart signal source is configured to receive second signals from a second sensor. The second sensor monitors a different physiological characteristic than the first sensor. The second heart signal source is configured to generate a second heart rate based on the second signals. The alarm algorithm is configured to receive the first and second heart rate, to determine the most accurate of the heart rates, and to only generate a heart rate limit alarm signal when the most accurate heart rate is outside a predetermined limit.

According to still another exemplary embodiment, a method of selecting physiological data from a plurality of physiological data sources includes providing first physiological data comprising a first measurement of a physiological trait and providing second physiological data comprising a second measurement of the physiological trait. The first and second measurements are based on different physiological characteristics. The method further includes selecting one of the first and second measurements as the output data for the physiological trait based on at least one of the first physiological data and the second physiological data.

BRIEF DESCRIPTION OF THE DRAWINGS

The invention will become more fully understood from the following detailed description, taken in conjunction with the accompanying drawings, wherein like reference numerals refer to like parts, and in which.

DETAILED DESCRIPTION OF EXEMPLARY EMBODIMENTS

Figure 1:
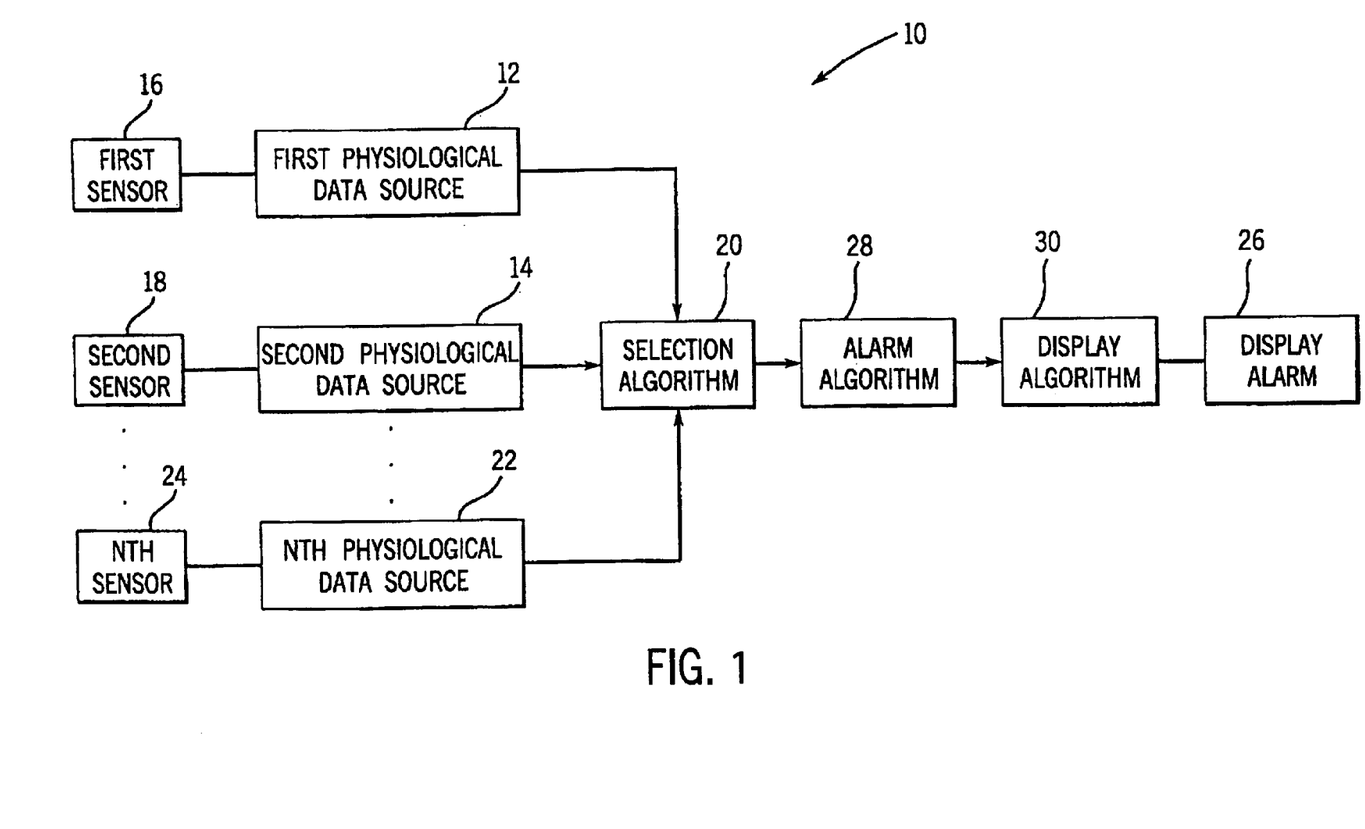
FIG. 1 is a block diagram of a system for selecting physiological data from a plurality of physiological data sources, according to an exemplary embodiment.

Referring first to FIG. 1, a system 10 for selecting physiological data from a plurality of physiological data sources is shown. System 10 may be part of a patient monitor for monitoring one or physiological traits (e.g., heart rate, respiratory rate, blood sugar levels, blood cell count, etc.). System 10 may be operable in a GE Marquette Medical Systems DASH 3000 Monitor, or other patient monitors.

System 10 includes a plurality of physiological data sources 12, 14 which are coupled to respective physiological sensors 16, 18. Sensors 16, 18 are placed on or in the vicinity of a patient to be monitored and are configured to read different physiological characteristics of the patient. For example, sensor 16 can measure the patient's electrocardiogram (ECG), and sensor 18 can measure the patient's invasive arterial blood pressure (IBP) or pulse oximetry ($SpO_2$). Alternatively, sensors 16, 18 can monitor other physiological characteristics of a patient. In this exemplary embodiment, the same physiological trait (e.g., heart rate) can be determined based on sensing different physiological characteristics (ECG, IBP, $SpO_2$) of the patient, making at least some of the data from sensors 16, 18 redundant.

Physiological data sources 12, 14 include software algorithms operable on a computer processing circuit or device (e.g., a microprocessor, a microcontroller, an application-specific integrated circuit (ASIC), etc.) including sufficient memory and interface circuitry to interface with sensor 16, 18. Physiological data sources 12, 14 preferably include algorithms which are operable independent of each other to arrive at one or more physiological data based on signals from respective sensors 16, 18. The physiological data provided by each of physiological data sources 12, 14 may include raw data from sensors 16, 18, filtered data, statistical derivations of data from sensor 16, 18, binary flags indicating predetermined conditions are met, or other events or conditions based on signals from sensors 16, 18.

Physiological data source 12 is configured to provide a first measurement of a physiological trait based on the physiological characteristic to a selection algorithm 20. Physiological data source 14 is configured to provide a second measurement of the same physiological trait based on a different physiological characteristic than that measured by physiological data source 14, and to provide the second measurement to selection algorithm 20. As indicated by Nth physiological data source 22 and Nth sensor 24, additional physiological data may be sensed and provided to selection algorithm 20.

Selection algorithm 20 is configured to receive first and second physiological data from sources 12, 14 including the first and second measurements of the physiological trait. Selection algorithm 20 is configured to select one of the first and second measurements as the output data for the physiological trait and to provide the output data as an output for subsequent processing. In this exemplary embodiment, the output data is provided to a display/alarm 26, which may include a cathode ray rube (CRT) display, liquid crystal display (LCD), or other display system, and may further include speakers, a wireless transmitter, or other output devices.

Selection algorithm 20 bases the selection of either the first measurement or the second measurement on the physiological data received from at least one of sources 12 and 14. Exemplary embodiments of this selection process will be described hereinbelow. In this exemplary embodiment, selection algorithm 20 is a ruled-based algorithm configured to select the first or second measurement of the physiological trait from sources 12, 14 and to provide the selected physiological measurement to display/alarm 26. Selection algorithm 20 may select the measurement having the greatest accuracy as the output data.

Figure 5:
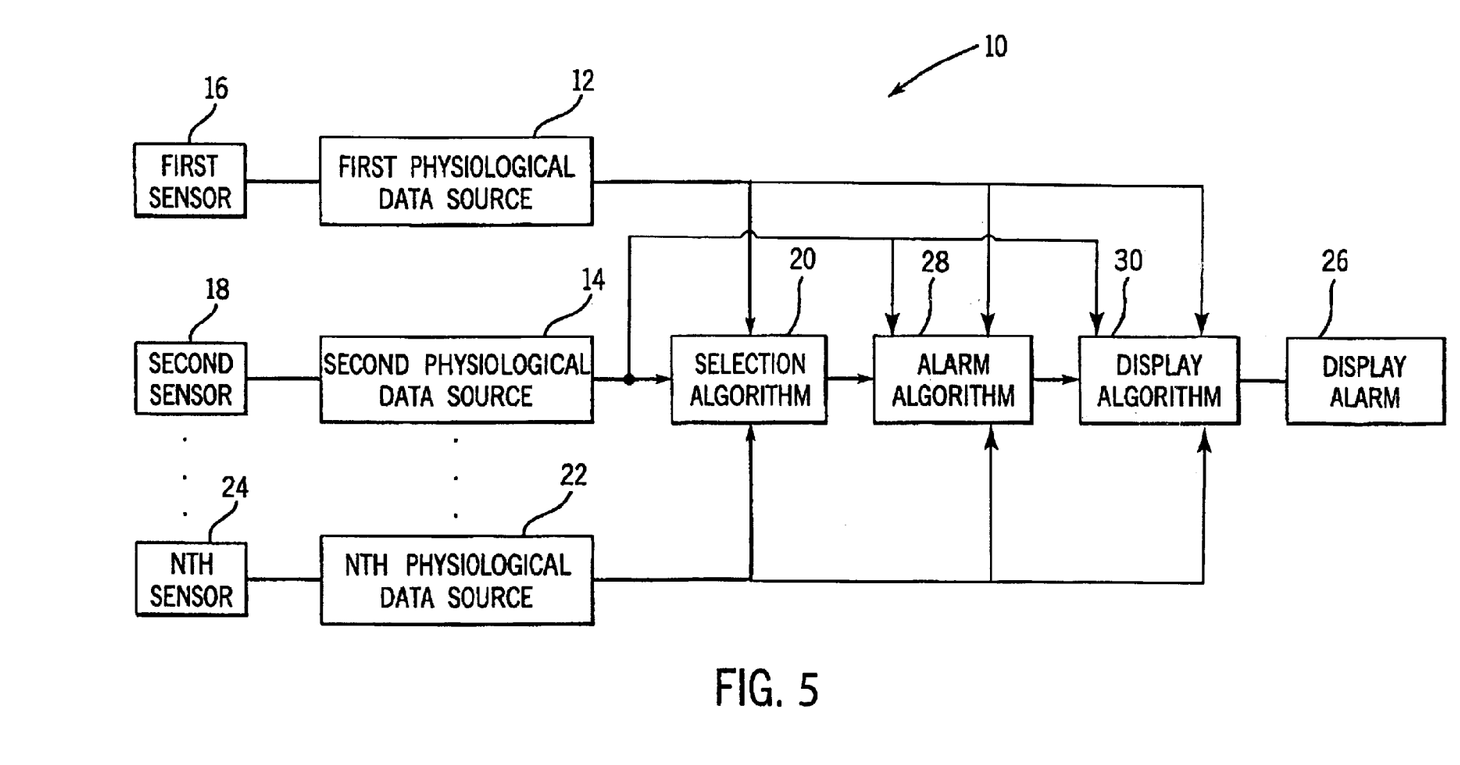
FIG. 5 is a block diagram of a system for selecting physiological data from a plurality of physiological data sources, according to an alternate embodiment.

System 10 may further include an alarm algorithm 28 configured to receive the output data from selection algorithm 20, to compare the output data to predetermined alarm conditions, and to provide an alarm signal to display/alarm 26 based on the comparison. In this manner, selection algorithm 20 provides the most accurate measurement of the physiological trait to alarm algorithm 28 so that false positive alarms are reduced. System 10 may further include a display algorithm 30 configured to receive the output data and/or the alarm signal from selection algorithm 20 and/or alarm algorithm 28 and to generate display signals on display/alarm 26. Selection algorithm 20 may be configured to provide a plurality of physiological data from sources 12, 14 to display algorithm 30 for display on display/alarm 26. In this manner, system 10 may be configured to display both the first measurement and second measurement of the physiological trait, and may further be configured to display the output data from selection algorithm 20, the output data including the more accurate of the first and second measurement. In various alternative embodiments, the function of selection, alarm determination, and display generation may be provided by one or more of algorithms 20, 28, and 30 (shown in FIG. 5).

Figure 2:
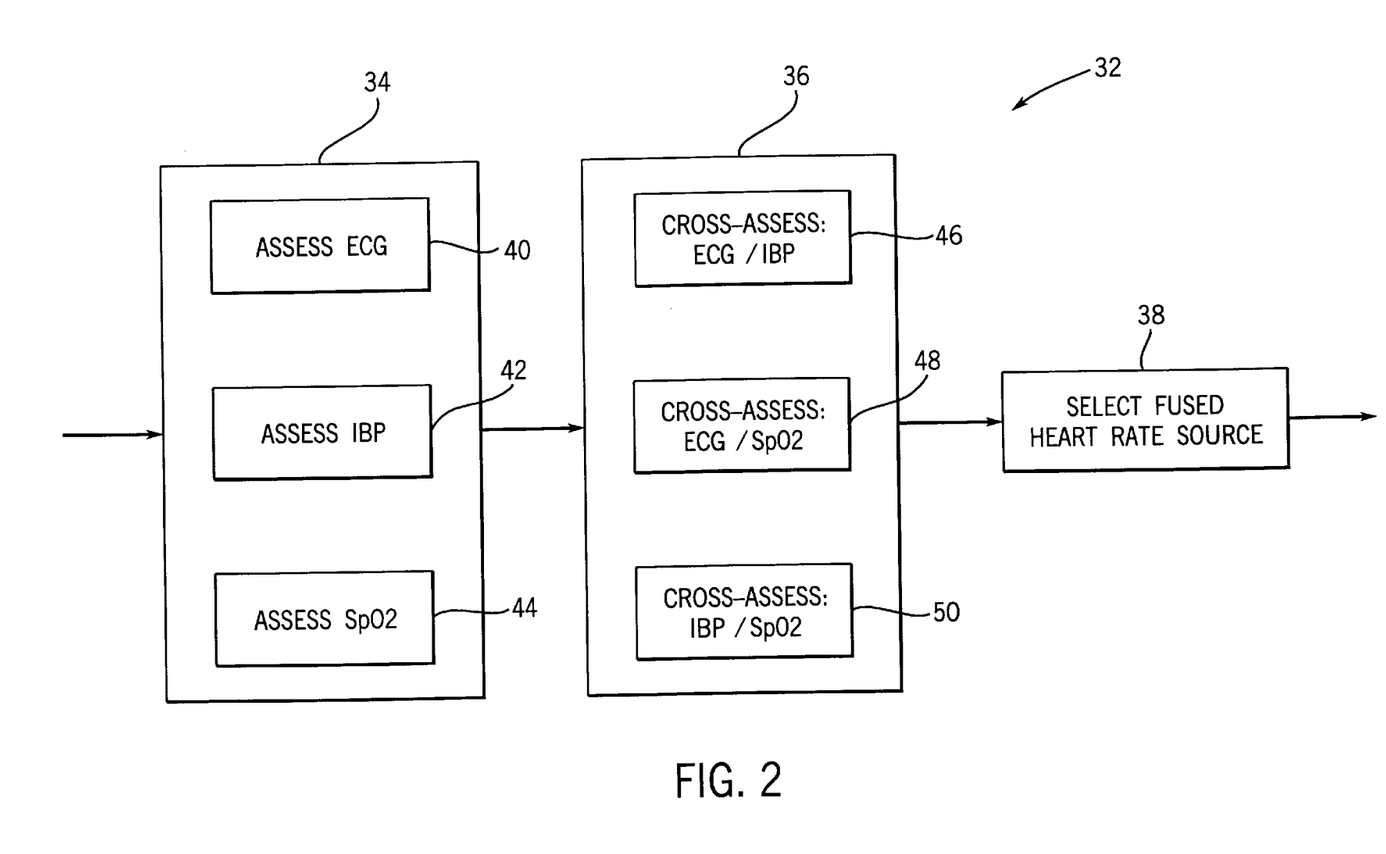
FIG. 2 is a block diagram of a system for selecting physiological data from a plurality of physiological data sources, according to another exemplary embodiment.

Referring now to FIG. 2, a block diagram of a system 32 for selecting physiological data from a plurality of physiological data sources is shown according to another exemplary embodiment. System 32 includes a physiological signal assessment algorithm 34, a physiological signal cross-assessment algorithm 36, and a selection algorithm 38. In this exemplary embodiment, system 32 is configured for monitoring signals relating to the physiological characteristic of heart rate. System 32 is configured to select one of the heart rates from assessment algorithm 34 as the output heart rate.

Assessment algorithm 34 includes an ECG assessment algorithm 40, and IBP assessment algorithm 42, and an $SpO_2$ assessment algorithm 44. Each of algorithms 40, 42, and 44 receives signals from respective physiological sensors and assesses the respective signals to provide one or more physiological data. The physiological data from each of algorithms 40, 42, and 44 includes a heart rate. The physiological data may include additional data. For example, ECG assessment algorithm 40 is configured to output an arrhythmia status flag indicating whether an arrhythmia condition has been identified by algorithm 40. IBP assessment algorithm 42 is configured to provide an invasive blood pressure artifact signal indicating if an artifact is identified in the IBP signal, a disconnect status signal indicating a disconnection of the IBP sensor from the patient, and mean systolic and diastolic pressures. $SpO_2$ assessment algorithm 44 is configured to output an oxygen saturation. Algorithms 40, 42, and 44 may provide one of more of these and other physiological data to cross-assessment algorithm 36.

Cross-assessment algorithm 36 is a rule-based algorithm configured to receive heart rates, and other physiological data from each of algorithms 40, 42, and 44 and to cross-assess one or more of the physiological data against one another. Cross-assessment algorithm 36 includes an ECG/IBP cross-assess algorithm 46, and ECG/SpO$_2$ cross-assess algorithm 48, and an IBP/SpO$_2$ cross-assess algorithm 50. Algorithms 46, 48, and 50 compare one or more of the physiological data from the data sources identified to determine which of the data sources provides a heart rate most suitable for the output data. For example, algorithms 46, 48 and 50 may be configured to identify the heart rate having the greatest accuracy. In this exemplary embodiment, the ECG heart rate is assumed to be the most accurate and is only superceded in the output data by the IBP heart rate or SpO$_2$ heart rate if one of the IBP or SpO$_2$ heart rates provide greater accuracy. Algorithm 50 evaluates which of the IBP heart rate and SpO$_2$ heart rate has the greatest accuracy.

Selection algorithm 38 selects the data source having the most accurate heart rate and provides this heart rate as output data to subsequent processing systems, such as an alarm algorithm, display algorithm, and/or a display/alarm.

Figure 3:
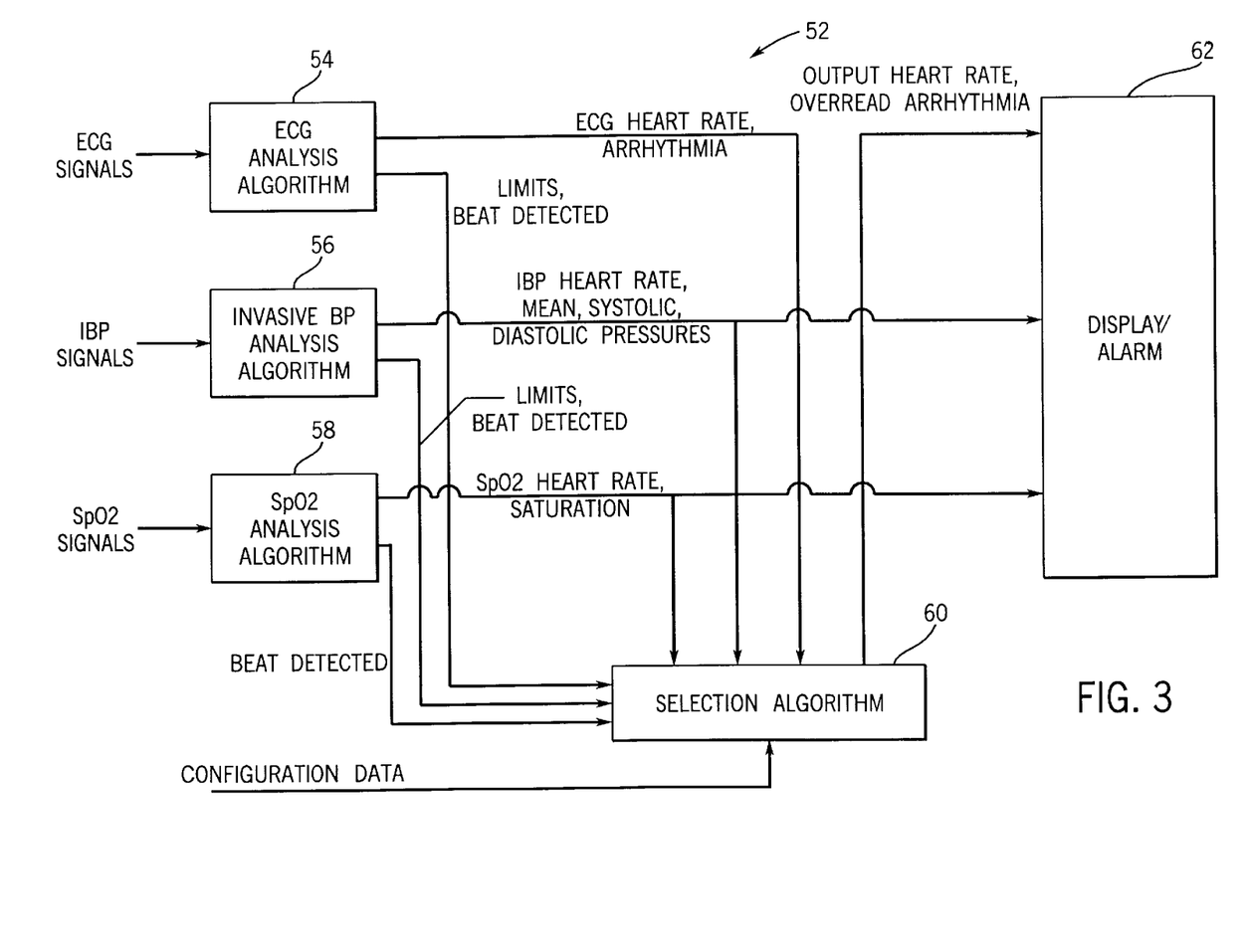
FIG. 3 is a block diagram of a system for selecting physiological data from a plurality of physiological data sources, according to yet another exemplary embodiment.

Referring now to FIG. 3, a block diagram of a system for selecting physiological data from a plurality of physiological data sources according to another exemplary embodiment is illustrated. System 52 illustrates an embodiment in which an improved heart rate accuracy is provided, and improved heart rate limit and arrhythmia alarms are also provided. System 52 includes an ECG analysis algorithm 54, an IBP analysis algorithm 56, and an SpO$_2$ analysis algorithm 58. Each of algorithms 54, 56, and 58 is configured to receive signals from respective sensors and to process the respective signals to provide physiological data to a selection algorithm 60 and to a display/alarm 62. System 52 may further include an alarm algorithm and a display algorithm, some or all of which may be operable in selection algorithm 60 and/or display/alarm 62.

ECG analysis algorithm 54 is configured to receive ECG signals and to process the ECG signals and provide physiological data including an ECG heart rate, an arrhythmia indicator, high and low alarm limits, and a beat detected signal to selection algorithm 60. IBP analysis algorithm 56 is configured to receive IBP signals and to process the IBP signals to provide physiological data including IBP heart rate, mean, systolic and diastolic pressures, high and low alarms limits, and a beat detected signal to selection algorithm 60. IBP analysis algorithm 56 further provides IBP heart rate, mean, systolic, and diastolic pressures directly to display/alarm 62 for display. SpO$_2$ analysis algorithm 58 receives SpO$_2$ signals and processes the SpO$_2$ signals to provide physiological data including an SpO$_2$ heart rate, oxygen saturation, and a beat detected signal to selection algorithm 60. SpO$_2$ analysis algorithm 58 further provides the SpO$_2$ heart rate and oxygen saturation to display/alarm 62 for display thereon. Selection algorithm 60 is further configured to receive configuration data, including whether "pace mode" processing is required (i.e., if the patient has a pace maker), whether "neo" mode processing is required for a neonate, unit type (OR, ICU, NICU), patient age, etc.

Figure 4:
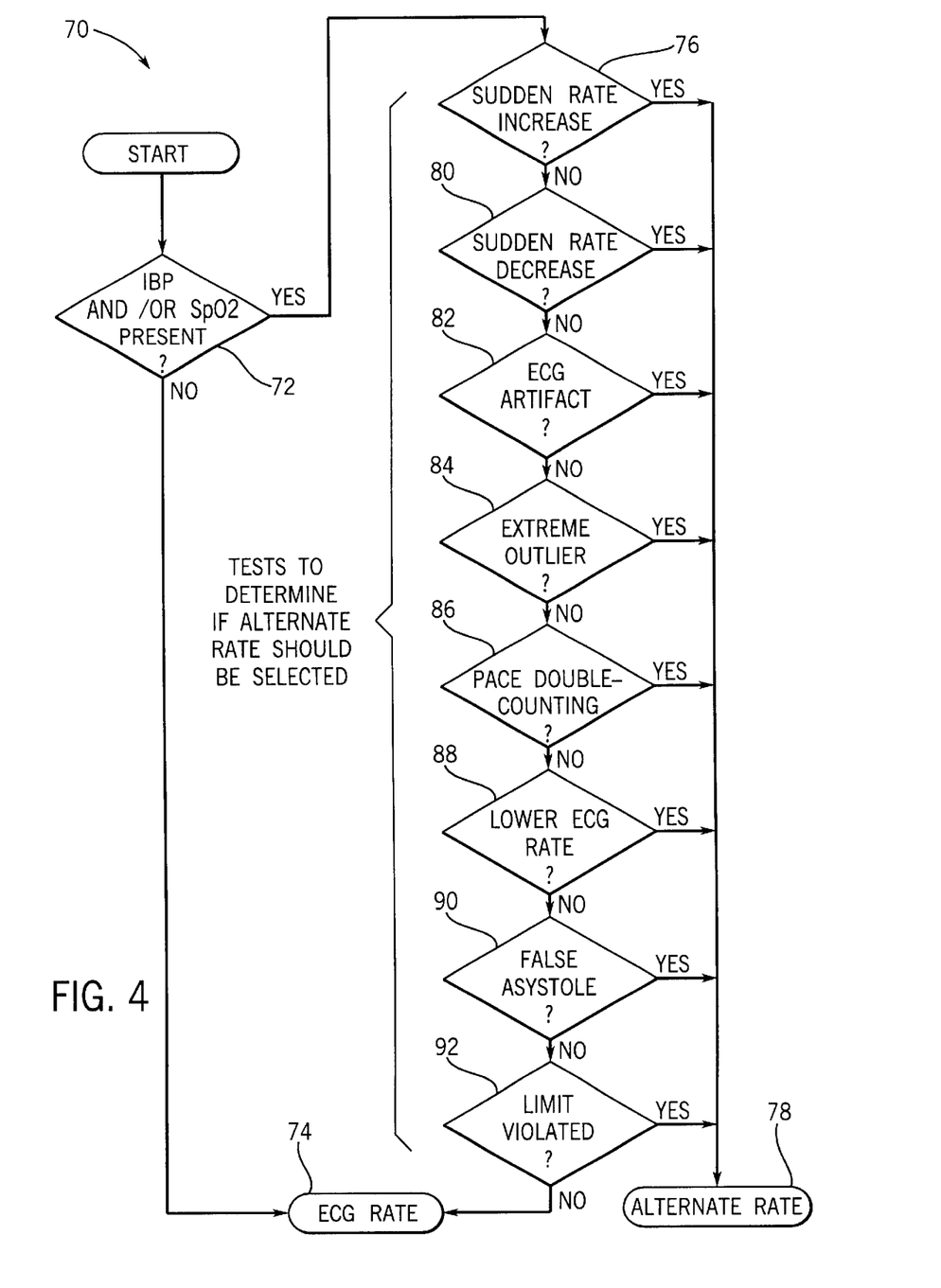
FIG. 4 is a flowchart of a method of selecting physiological data from a plurality of physiological data sources operable in the selection algorithm of FIG. 3, according to an exemplary embodiment.

Selection algorithm 60 is operable according to the exemplary method shown in FIG. 4 to select from among the ECG heart rate, IBP heart rate, and SpO$_2$ heart rate and to provide the selected heart rate to provide to display/alarm 62. Selection algorithm 60 is further configured to provide a more accurate arrhythmia alarm to display/alarm 62 based on the physiological data received. Selection algorithm 60 is designed as a separate software module in this embodiment, suitable for use in embedded systems, and may further include an interface to support data exchange and algorithm configuration and control. The physiological data shown in FIG. 3 is provided to selection algorithm 60 at a minimum of once every two seconds.

As mentioned, selection algorithm 60 is configured to provide one of ECG heart rate, IBP heart rate, and SpO$_2$ heart rate as an output heart rate, and further to provide an overread arrhythmia (i.e. a verification or qualification of a machine's determination of arrhythmia) to display/alarm 62. According to one alternative embodiment, selection algorithm 60 may be configured to turn off the output heart rate and overread arrhythmia functions in response to operator input or other configuration data, in which case, the ECG heart rate and/or arrhythmia status are merely passed through selection algorithm 60 to display/alarm 62.

Referring now to FIG. 4, a method 70 of selecting physiological data from a plurality of physiological data sources will be described according to an exemplary embodiment. Method 70 begins at step 72 by checking to see if physiological data is being received by an IBP data source and/or an SpO$_2$ data source. If no data is available from an IBP or SpO$_2$ data source, selection algorithm 60 uses data directly from an ECG data source as indicated at step 74. If either an IBP or SpO$_2$ data source is present, the method proceeds to steps 76–92 to determine if a heart rate other than the ECG heart rate should be selected. Method 70 is used to determine which of ECG heart rate, IBP heart rate, and SpO$_2$ heart rate are to be used as the output heart rate and for alarm generation. As shown, when an ECG heart rate is available, it is used as the default rate and an alternate rate is selected only when the ECG rate is suspect and an alternate rate is deemed a credible substitute. Steps 76–92 illustrate tests or conditions that are completed to determine whether the ECG rate or alternate rate should be selected as the output heart rate. In all test cases, if the ECG heart rate is not deemed credible, the IBP heart rate is considered next before the SpO$_2$ rate, unless otherwise indicated. Steps 76–92 are merely exemplary of the types of rule-based comparisons that can be applied to improve the heart rate limit alarm functions and algorithm alarm functions.

At step 76, if the ECG heart rate increases at a rate exceeding a predetermined increase rate, but the hemodynamic rates (e.g., IBP heart rate and SpO$_2$ heart rate) remain substantially the same, it is concluded that the sudden rate increase is due to artifactual QRS detections and an alternate rate is selected. In this exemplary step, the SpO$_2$ rate is used only if the IBP heart rate is not "O.K." as determined by selection algorithm 60 and the ECG Artifact flag is set. IBP is not "O.K." if HR$_{IBP}$≦0 or mean BP≦0, or (systolic diastolic)≦0.

If no sudden rate increase is detected at step 76, the method proceeds to step 80 to check for a sudden rate decrease. At step 80, if the ECG heart rate decreases at a rate exceeding a predetermined decrease rate, and the IBP rate remains substantially the same, the IBP rate will be selected as the alternate rate. The SpO$_2$ rate will not be selected by this test.

At step 82, the method checks the ECG "artifact" flag to determine if the flag is set. If the artifact flag is set and the ECG rate is not substantially constant, the IBP rate will be selected at step 78. The SpO$_2$ will not be selected by this test.

At step 84, the method identifies the presence of an ECG rate extreme outlier (i.e., the ECG heart rate is well outside the normal distribution of recently observed rates —for example, one, two or three times the standard deviation—of recently observed rates). Most ECG rate extreme outliers will be identified by the sudden rate increase and sudden rate decrease steps 76, 80. Step 84 checks any remaining outlying data points and selects an alternate rate. If the alternate rate is substantially constant and is also closer to the average ECG heart rate over recently observed rates (e.g., those rates having been processed by filtering with a time constant at 20 seconds), then the alternate rate will be selected at step 78 for display and alarm generation functions.

At step 86, if "pace mode" processing is enabled in algorithm 60, and the ECG heart rate is approximately twice the heart rate of either or both of the hemodynamic heart rates, and the hemodynamic heart rate is greater than 50 beats per minute and is substantially constant, one of the hemodynamic rates will be picked as the alternate rate. The test in step 86 may be disabled under select circumstances, such as, if the patient's age is less than 10 years or if system 10 is in "neo" mode.

At step 88, if the ECG heart rate is lower than the IBP heart rate, exhibits a much greater variability then the IBP heart rate, and if the IBP heart rate is substantially constant, the IBP heart rate will be selected as the alternate rate. The $SpO_2$ heart rate will not be selected by this test.

At step 90, if the ECG rate is zero and either of the hemodynamic parameters has a substantially constant positive heart rate, one of the hemodynamic rates is selected as the alternate rate. This test helps identify a false asystole condition and prevents a false asystole alarm if a normal heart rate is read by the hemodynamic sensors.

At step 92, if the ECG heart rate violates a high rate limit or a low rate limit, as provided by ECG analysis algorithm 54, if a hemodynamic parameter shows a substantially constant positive heart rate, and the ECG heart rate is not substantially constant and the hemodynamic heart rate is closer to the last ECG rate than the current ECG rate, a hemodynamic data source is selected for the heart rate.

Selection algorithm 60 is further configured to calculate one or more of mean and variance for the physiological data received from algorithms 54, 56, and 58 to assist in the selection of the optimal data source for output data. The selection algorithm 60 can determine "normal" physiological parameters for the patient based on calculations of mean and variance. Selection algorithm 60 may calculate whether a new heart rate value differs "significantly" from a normal or expected value by calculating an estimate of the variance of the variable, and comparing the new heart rate value to one standard deviation (in which 68% of the input samples would fall), two standard deviations (in which 95% of the input samples would fall), or three standard deviations (in which 99.7% of the input samples would fall). In this exemplary embodiment, selection algorithm 60 calculates mean and variance values for ECG heart rate, IBP heart rate, IBP mean pressure, IBP pulse pressure (i.e. the difference between the systolic and diastolic pressures), $SpO_2$ heart rate, and $SpO_2$ saturation. For each of these variables, the following values are computed with each new data: the difference between the new value and the mean, the percent difference between the new value and the mean, and the number of standard deviations between the new value and the mean.

Numerous advantages are provided by this exemplary method. For example, when the heart rate from the ECG data source is inaccurate or unreliable, selection algorithm 60 is configured to select a better heart rate from the hemodynamic heart rate sources. This provides the advantage of a more accurate heart rate which can be displayed on display/alarm 62 along with the heart rates from algorithms 54, 56, and 58. According to another advantage, selection algorithm 60 is configured to receive an ECG heart rate and a hemodynamic heart rate, to determine which of the ECG heart rate and hemodynamic heart rate is most accurate, and to provide an alarm signal to display/alarm 60 when the most accurate heart rate is outside a predetermined limit (e.g., a maximum heart rate or minimum heart rate). This advantageous aspect prevents false positive alarms due to ECG sensor errors or artifacts when a patient does not have an excessively high or low heart rate. According to yet another advantageous aspect, when ECG analysis algorithm 54 indicates that an arrhythmia has been detected, selection algorithm 60 is configured to prevent an alarm signal if the hemodynamic heart rate data indicates that no arrhythmia condition exists (e.g., the hemodynamic heart rate sensors indicate that heart rate is steady and constant). This feature prevents false positive arrhythmia alarms. Other alarm processing conditions will also be improved by utilizing a more accurate heart rate from among the ECG heart rate, the IBP heart rate, and the $SpO_2$ heart rate.

Selection algorithm 60 may further be configured to provide an automatic asystole alarm for patients whose heart has stopped responding to an electronic pacing device. This condition cannot always be readily determined by examination of ECG only. However, selection algorithm 60 is configured to monitor heart rate data from hemodynamic heart rate sensors to detect the asystole condition.

According to a further advantageous aspect of some embodiments of the method and system described herein, because the heart rate from one of algorithms 54, 56, and 58 is used without subsequent filtering or processing, no additional processing delays are added in the selection process. Furthermore, the use of existing heart rate estimates increases the likelihood of acceptance by clinicians. A further advantage is that errors in ECG heart rate due to a patient having a relatively low amplitude ECG, or a patient that rolls over in bed or loses a signal on an ECG sensor is compensated for by the hemodynamic sensors until the ECG sensors can be repositioned or replaced.

Selection algorithm 60 may further be configured to detect an asystole condition or other arrhythmia in a patient even when the patient has an electronic pacemaker. In some circumstances, a patient monitor will be unable to detect an asystole condition on a patient in the presence of an electronic pacemaker artifact because the pacemaker continues to fire at the paced rate in spite of the asystole condition. Selection algorithm 60 may be configured to monitor one or more of the hemodynamic parameters to identify the asystole condition. If selection algorithm 60 identifies that blood pressure drops at a particular rate or to a particular number, even though ECG heart rate may remain steady, selection algorithm 60 is configured to generate an asystole alarm signal and provide the alarm signal to display/alarm 62.

Advantageously, while an $SpO_2$ and an IBP sensor have been described herein as data sources which are redundant to an ECG data source for the trait of heart rate, in alternative embodiments, other sensors which provide a continuous estimate of heart rate could also be used.

EXAMPLE

Clinical testing of the system and method described above with reference to FIGS. 3 and 4 was performed on 55 patients totaling 964 hours of monitoring time. The patient population included adults, pediatrics and neonates, both paced and non-paced. The records were beat-by-beat annotated on a Marquette Mars Holter Review workstation which allowed for the creation of referenced heart rates for all patients. The recorded ECG rate was compared to the referenced rate to establish baseline values for heart rate accuracy and heart rate limit alarm accuracy (sensitivity, positive predicted value). These clinical data records were then retrospectively processed by the new software algorithm and the results again compared to the reference rate to yield corresponding statistics for comparison.

The resulting sensitivity and positive predictive value (PPV) for heart rate limit alarms were as follows:

|  | Low HR Alarms | | High HR Alarms | |
| --- | --- | --- | --- | --- |
|  | Sensitivity | PPV | Sensitivity | PPV |
| ECG Only | 96 | 58 | 93 | 86 |
| Selection Algorithm | 94 | 84 | 93 | 88 |

The chart above indicates that the positive predicted value for the low heart rate alarms was improved substantially using the system and method described in FIGS. 3 and 4. A slight improvement was also found in the positive predictive value of the high heart rate alarm.

In addition, the number of false asystole and/or false ventricular fibrillation alarms on this data is reduced by the system from 19 (ECG only) to 2 (selection algorithm 60).

While the exemplary embodiments illustrated in the FIGS. and described above are presently preferred, it should be understood that these embodiments are offered by way of example only. For example, the teachings herein may be applied to various physiological signals to identify inconsistencies between sensors sensing the same physiological trait and to use a selection process to choose the sensor having the greatest reliability. Such systems would utilize a first sensor sensing a first physiological characteristic to arrive at information about the physiological trait and a second sensor sensing a different physiological characteristic than the first sensor to arrive at information about the physiological trait. Accordingly, the present invention is not limited to a particular embodiment, but extends to various modifications that nevertheless fall within the scope of the appended claims.

What is claimed is:

1. A system for selecting physiological data from a plurality of physiological sources, the system implemented on a computer-readable medium having program code recorded thereon for execution in a computer, the program code comprising:

a first physiological data source configured to provide first physiological data, wherein the first physiological data comprises a first measurement of a physiological trait;

a second physiological data source configured to provide second physiological data, wherein the second physiological data comprises a second measurement of the physiological trait, wherein the first and second measurements are based on different physiological characteristics; and a selection algorithm configured to receive the first and second physiological data and to select one of the first and second measurements as the output data for the physiological trait based at least on the first physiological data exceeding a predetermined limit and the second physiological data.

2. The system of claim 1, further comprising an alarm algorithm configured to receive the output data, to compare the output data to a predetermined alarm condition, and to provide an alarm signal based on the comparison.

3. The system of claim 1, further comprising a display algorithm configured to receive the output data and to generate display signals for simultaneous display of the output data and at least one of the first and second measurements of the physiological trait.

4. The system of claim 1, wherein the first physiological data further comprises a statistical function of the first measurement of the physiological trait.

5. The system of claim 1, wherein the physiological trait comprises patient heart rate.

6. The system of claim 5, further comprising:

an ECG sensor coupled to the first physiological data source wherein the first physiological data source is configured to receive signals from the ECG sensor; and one of an SpO2 sensor and an IBP sensor coupled to the second physiological data source, wherein the second physiological data source is configured to receive signals from one of the SpO2 sensor and the IBP sensor.

7. The system of claim 6, wherein the selection algorithm is configured to select the second measurement as the output data in response to an increase or decrease in a heart rate from the first measurement beyond the predetermined limit and in response to a substantially constant heart rate from the $SpO_2$ or IBP sensor.

8. A system for improving the accuracy of an arrhythmia detection algorithm, the system implemented on a computer-readable medium having program code recorded thereon for execution in a computer, the program code comprising:

an ECG data source configured to receive ECG signals and to generate ECG heart rate data based on the received ECG signals;

an arrhythmia detection algorithm configured to receive ECG heart rate data and to detect an arrhythmia condition;

a hemodynamic heart rate data source configured to receive hemodynamic heart rate signals and to generate hemodynamic heart rate data based on the received signals; and an alarm algorithm configured to receive the ECG heart rate data and the hemodynamic heart rate data, to select one of the ECG heart rate data and the hemodynamic heart rate data as the most accurate of the heart rates based on at least the ECG heart rate data exceeding a first predetermined limit and to provide and alarm based on the detected arrhythmia condition and the hemodynamic heart rate data.

9. The system of claim 8, wherein, when an arrhythmia condition is detected by the arrhythmia detection algorithm, the alarm algorithm is configured to prevent the alarm signal if the hemodynamic heart rate indicates that no arrhythmia condition exists.

10. The system of claim 8, further comprising an IBP sensor or $SpO_2$ sensor coupled to the hemodynamic heart rate data source, wherein the hemodynamic heart rate data source receives signals from the IBP sensor or $SpO_2$ sensor.

11. The system of claim 8, wherein the system operates in a real-time monitoring environment.

12. The system of claim 8, wherein the arrhythmia condition is an asystole condition.

13. A system for improving the accuracy of a heart rate limit alarm, the system implemented on a computer-readable medium having program code recorded thereon for execution in a computer, the program code comprising:

a first heart rate signal source configured to receive first sensor signals and to generate a first heart rate based on the first sensor signals;

a second heart signal source configured to receive second sensor signals, wherein the second sensor signals measure a different physiological characteristic than the first sensor signals, wherein the second heart signal source is configured to generate a second heart rate based on the second sensor signals; and an alarm algorithm configured to receive the first and second heart rate, to select one of the first heart rate and the second heart rate as the most accurate of the heart rates based on at least the first heart rate exceeding a first predetermined limit, and to only generate a heart rate limit alarm signal when the most accurate of the heart rates is outside a second predetermined limit.

14. The system of claim 13, wherein the alarm algorithm is configured to select the second heart rate as the most accurate heart rate when the first heart rate increases at a rate exceeding the first predetermined limit and the second heart rate remains substantially constant.

15. The system of claim 13, wherein the alarm algorithm is configured to select the second heart rate as the most accurate heart rate when the first heart rate decreases at a rate exceeding the first predetermined limit and the second heart rate remains substantially constant.

16. The system of claim 13, further comprising:

a first sensor coupled to the first heart rate signal source, wherein the first heart rate signal source is configured to receive first sensor signals from the first sensor:

a second sensor coupled to the-second heart rate signal source, wherein the second heart rate signal source is configured to receive second sensor signals from the second sensor;

wherein the first sensor is an ECG sensor and the second sensor is a hemodynamic heart rate sensor.

17. The system of claim 16, wherein the hemodynamic heart rate sensor is an $SpO_2$ sensor or an IBP sensor.

18. A method of selecting physiological data from a plurality of physiological data sources, comprising:

providing first physiological data comprising a first measurement of a physiological trait;

providing second physiological data comprising a second measurement of the physiological trait, wherein the first and second measurements are based on different physiological characteristics; and selecting one of the first and second measurements as the output data for the physiological trait based at least on the first physiological data exceeding a predetermined limit and the second physiological data.

19. The method of claim 18, further comprising comparing the output data to a predetermined alarm condition and providing an alarm signal based on the comparison.

20. The method of claim 18, further comprising generating display signals for simultaneous display of the output data and at least one of the first and second measurements of the physiological trait.

21. The method of claim 18, wherein the physiological trait comprises patient heart rate.

22. The method of claim 21, further comprising:

receiving ECG signals from an ECG sensor and generating the first physiological data based on the ECG signals; and receiving hemodynamic heart rate signals from a hemodynamic heart rate sensor and generating the second physiological data based on the hemodynamic heart rate signals.

* * * * *